(12) United States Patent
Reid, II et al.

(10) Patent No.: US 6,619,321 B2
(45) Date of Patent: Sep. 16, 2003

(54) STREAM SWITCHING SYSTEM

(75) Inventors: Kenneth E. Reid, II, Oxford, AL (US); Frank A. Ruiz, Greenwell Springs, LA (US)

(73) Assignee: Parker-Hannifin Corporation, Cleveland, OH (US)

( * ) Notice: Subject to any disclaimer, the term of this patent is extended or adjusted under 35 U.S.C. 154(b) by 36 days.

(21) Appl. No.: 09/931,337

(22) Filed: Aug. 16, 2001

(65) Prior Publication Data

US 2002/0020451 A1 Feb. 21, 2002

Related U.S. Application Data

(60) Provisional application No. 60/254,335, filed on Dec. 8, 2000, and provisional application No. 60/226,216, filed on Aug. 18, 2000.

(51) Int. Cl.$^7$ .............................................. F16K 11/22
(52) U.S. Cl. ................................ 137/625.27; 137/625.5
(58) Field of Search ...................... 137/625.66, 625.27, 137/625.5

(56) References Cited

U.S. PATENT DOCUMENTS

| | | | |
|---|---|---|---|
| 1,926,925 A | | 9/1933 | Wescott |
| 2,988,279 A | | 6/1961 | Irwin |
| 3,016,917 A | * | 1/1962 | Hunt ..................... 137/625.27 |
| 3,111,139 A | | 11/1963 | Beckett et al. |
| 3,158,164 A | | 11/1964 | Barton |
| 3,215,158 A | | 11/1965 | Bass et al. |
| 3,263,253 A | | 8/1966 | Symmons |
| 3,335,756 A | | 8/1967 | McPherson |
| 3,509,904 A | | 5/1970 | Olson |
| 3,563,131 A | | 2/1971 | Ridley |
| 3,654,960 A | | 4/1972 | Kiernan |
| 3,731,905 A | * | 5/1973 | Piet ............................ 251/333 |

(List continued on next page.)

FOREIGN PATENT DOCUMENTS

| | | |
|---|---|---|
| FR | 1 325 312 | 3/1963 |
| SU | 720215 | 3/1980 |

OTHER PUBLICATIONS

Documentation from Autoflow Products Co., copyrighted 1998.

Whitey Product Release for "T2 Series Valves" copyrighted 1995, 1995.

*Primary Examiner*—John Fox
(74) *Attorney, Agent, or Firm*—Christopher H. Hunter

(57) ABSTRACT

A stream selector for a process analyzer prevents contamination of one sample from previous samples without requiring a common outlet header. The stream selector includes a valve manifold having a base plate and a series of valve modules individually removeably attached to the base plate. The base plate includes all the process connections for the fluid lines. Each valve module includes a module body with a pair of valve assemblies. The valve assemblies in each module are operated simultaneously through a common actuation passage. A poppet valve in each valve assembly has a valve head with a double-seated seal. The double seated seal controls the flow of fluid through a vent passage in the valve body; and between inlet and outlet passages in the valve body. The outlet passage from one valve assembly is fluidly-connected to the inlet passage of an adjacent valve assembly to create a double-block and bleed configuration. The downstream valve assembly is then connected to the process analyzer. If additional valve module(s) are used, the outlet of the downstream valve assembly in the first module can be routed through the vent passage of the downstream valve assembly of the second module, and so on. A cover encloses the valve assembly in each valve module. The cover is attached with a series of threaded bolts to the module body. At least some of the bolts fix the module body to the base plate. Removing the bolts allows individual modules to be removed from the base plate without removing adjacent modules.

7 Claims, 11 Drawing Sheets

U.S. PATENT DOCUMENTS

| | | |
|---|---|---|
| 4,011,888 A | 3/1977 | Whelchel et al. |
| 4,271,970 A | 6/1981 | Butler et al. |
| 4,334,785 A | 6/1982 | Blach |
| 4,615,353 A * | 10/1986 | McKee ............ 137/625.27 |
| 4,848,405 A | 7/1989 | Albrecht |
| 4,915,134 A * | 4/1990 | Toliusis et al. ........ 137/625.65 |
| 4,934,411 A | 6/1990 | Albrecht |
| 5,020,570 A | 6/1991 | Cotter |
| 5,207,545 A | 5/1993 | Kochanski |
| 5,305,788 A | 4/1994 | Mayeux |
| 5,361,805 A | 11/1994 | Mayeux |
| 5,558,129 A | 9/1996 | Mayeux |
| 5,561,956 A | 10/1996 | Englekirk et al. |
| 5,697,746 A | 12/1997 | Brown et al. |
| 5,927,337 A | 7/1999 | LaMantia |
| 6,152,175 A | 11/2000 | Itoh et al. |

* cited by examiner

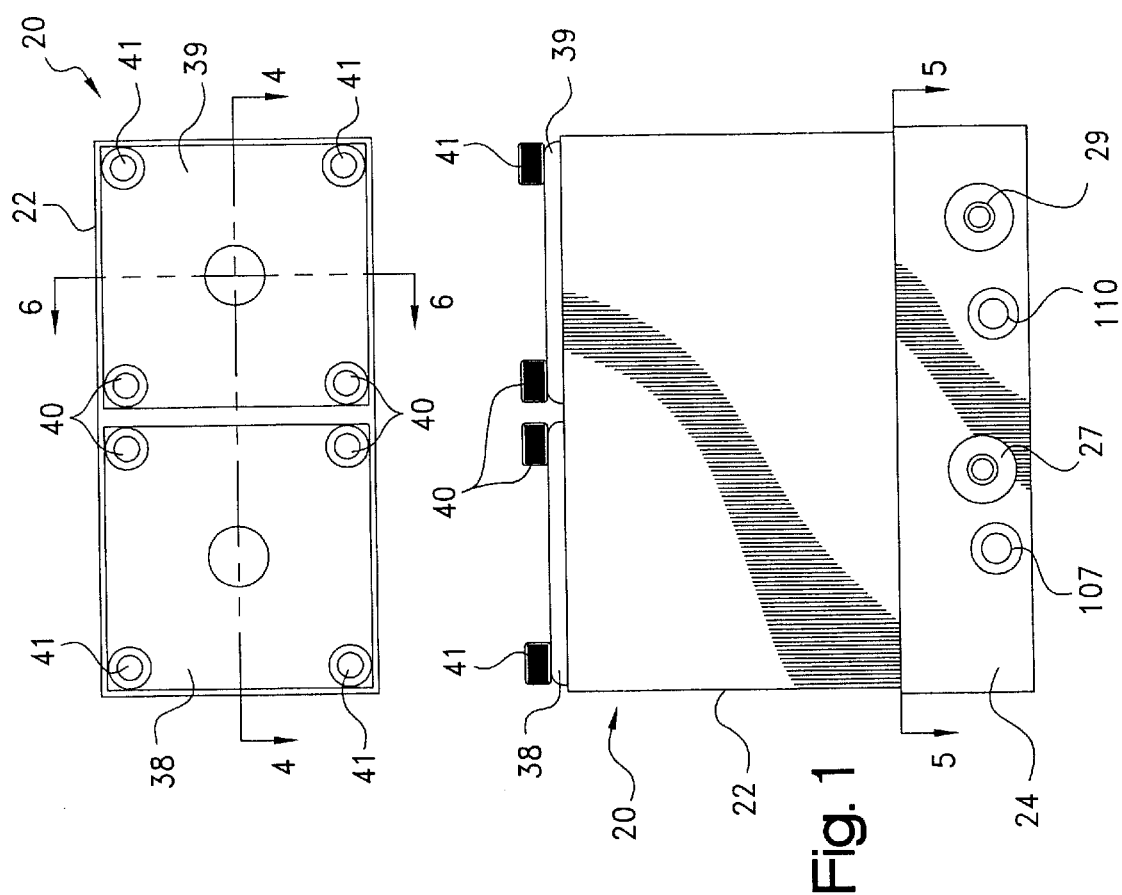

STREAM SWITCHING SYSTEM

CROSS-REFERENCE TO RELATED CASES

The present application claims the benefit of the filing date of U.S. Provisional Application Ser. No. 60/254,335; filed Dec. 8, 2000 and U.S. Provisional Application Ser. No. 60/226,216; filed Aug. 18, 2000.

FIELD OF THE INVENTION

The present invention relates generally to stream selectors for process analyzers.

BACKGROUND OF THE INVENTION

Stream selectors for process analyzers control the flow of fluid into the analyzer. The selector selects a single sample stream from multiple flow streams to pass on for analysis. This reduces the cost of analyzing multiple gas and liquid process streams in, e.g., a manufacturing or laboratory facility, as each analyzer is relatively expensive. The stream selector includes a series of valves which are typically electrically controlled. It is conventional practice to use a common outlet header connected to each valve to route the selected sample stream to the analyzer. It is important that only one sample is routed through the header to the analyzer at one time.

Important factors in analyzing process streams are i) cross-contamination of samples; ii) the size of the analyzer and associated components; and iii) the ease of installation, maintenance and repair of the analyzer. Cross-contamination of samples can be caused by leaking valves and/or dead volume (e.g., irregular passageways, large internal volumes, etc.) allowing contamination from previous samples. To overcome this problem, longer sample purge times and/or stream analysis have been used. However, this increases the time and cost associated with process analyzing, as well as requires the disposal of the greater purge volume. The size of the analyzer and related components is also an issue as large and bulky analyzers take up valuable panel space. The ease of installation, maintenance and repair of the analyzers is also an important consideration as there is a continuing demand to reduce the cost of the analyzers, and hence minimize the cost of the entire process system.

Certain stream selectors have been developed in an attempt to address some of these issues. For example, one stream selector is known which has a double block and bleed structure, where a set of three O-rings are carried on the head of a poppet valve. The poppet valve is normally biased into a closed (non-actuated) position by a compression spring, and can be moved into an open (actuated) position by pressurized gas or other means. The O-rings are designed to seal against opposed flat surfaces in the selector body to control the flow of fluid through the body. A first and second of the O-ring seals are located in grooves formed in one surface of the poppet valve head to seal against the inlet and outlet passages, respectively, when the selector is not actuated; while a third of the O-rings is loosely located around the poppet stem against the opposing surface of the poppet valve head and is designed to seal against a vent passage when the selector is actuated. An intermediate position is also provided, where the poppet valve head is in a position where all passages are open to completely purge any fluid in the selector system.

The double block and bleed structure is located in a valve module, and a series of such modules can be arranged adjacent one another to form the stream selector. A common outlet passageway (loop) is typically required between each valve module and the analyzer. The common outlet passageway allows purging of the passageway between different samples.

It is believed the O-ring seals in the selector described above can dry and crack, and/or swell and dislodge during repeated cycling, particularly in liquid applications. This can allow leak paths to occur between the inlet and outlet passages, and also through the vent passage. The selector also does not fully minimize the volume between the valve modules and the analyzer, as it requires an outlet loop. Providing an outlet loop increases the overall size of the selector, as well as adds additional cost to the system. The selector described above also requires the adjacent valve modules to be firmly pressed together and connected with long bolts extending horizontally through the modules. The bolts must be removed and all the modules disturbed if one of the modules is to be replaced. Since this can be quite an involved operation, the selector typically must be taken to a repair shop remote from the application. Process connections are also required for each module, so that the process connections for typically all modules must be disconnected when the one module is to be replaced. Leak paths can be introduced into the selector during all these disconnections and reconnections. Further, the stream selector of this design tends to be complex and include small C-clips and hidden roll pins, which makes assembly, maintenance, and repair, time-consuming and expensive.

It is also known to provide ball valves in stream switching, however, such ball valves are not known for their robust design during repeated cycling, and typically must be inspected and repaired or replaced at regular intervals. Selectors using such ball valves also tend to be quite large and require considerable space.

In light of the above, it is believed there is a demand for an improved stream selector for a process analyzer which prevents cross-contamination of samples, has a relatively small size, and has a simple valve structure which facilitates installation, maintenance and repair of the selector to minimize costs.

SUMMARY OF THE PRESENT INVENTION

The present invention provides a novel and unique stream selector for a process analyzer which prevents contamination of one sample from previous samples. The stream selector does not require a common outlet loop to connect the valves to the process analyzer, and has robust, long-lasting seals to prevent leakage. The stream selector also has modules of a compact size, which are relatively simple in construction and are individually and separately removeable. This reduces installation, maintenance and repair of the selector and minimizes costs of the entire system.

According to the present invention, the stream selector includes a series of base plates, and a series of valve modules which are individually removeably attached to the base plates. The base plates are connectable to each other via interengaging bolts, and include all the process connections for the fluid lines. This facilitates the assembly, maintenance and repair of the stream selector, as well as reduces the complexity of the valve modules.

Each valve module for the selector includes a module body with a pair of valve cavities. A valve assembly is received in each valve cavity. Each valve assembly includes a valve body enclosing a moveable piston, a valve bonnet, and a poppet valve. The valve assemblies are preferably operated simultaneously through a common actuation passage.

The poppet valve in each assembly extends through the bonnet and is connected to the piston, and moves in conjunction therewith. The poppet valve has a valve head with a double-seated seal. The double seated seal has on one side an annular plug seal received around the stem of the poppet valve for sealing to a first valve seat to control the flow of fluid through the vent passage in the valve body; and on the other side includes a solid cylindrical plug seal which seals to a second valve seat to control the flow of fluid between the inlet and outlet passages in the valve body. The first and second plug seals are preferably received in respective seal holders on the opposite surfaces of the head, and provide long-lasting, fluid-tight sealing over repeated cycling.

The outlet passage from one valve assembly in the module is routed to the inlet passage of the adjacent valve assembly in the module to create a double-block and bleed configuration. The downstream valve assembly in the module is then connected to the process analyzer. This configuration prevents downstream contamination of samples, and purges the valve module during each stream selection. No outlet loop is necessary to purge the modules.

If more than one valve module is used for the stream selector, the outlet of the downstream valve assembly in the first module is routed through the vent passage of the downstream valve assembly in the next module to purge residual fluid in the second module when the first module is actuated. This configuration is replicated for all the modules in the stream selector, and completely purges the selector of previous samples to prevent cross-contamination.

A cover encloses each valve assembly in the valve cavity of the module. The cover is attached by a series of threaded bolts to the module body. At least some of the bolts pass through the module body and fix the module body to the base plate. Loosening the bolts allows individual modules to be removed from the base plate without removing adjacent modules. This also allows the valve assemblies to be easily removed from each module.

As indicated above, the stream selector does not require a common outlet header (loop) to connect to the process analyzer. Rather, the outlet from the last module in the string of modules is connected directly to the analyzer. The previous process streams are fully vented before the introduction of a new process stream into the last module. The stream selector thereby prevents contamination of one sample with residual fluid from a previous sample, and has little dead volume. Still further, the stream selector has a compact size, and is relatively simple in construction. This also reduces installation, maintenance and repair costs. The seal plugs of the poppet valve are robust, long-lasting components that withstand repeated cycling without leaking. The modules each easily connect into and disconnect from the base plates, which carry all the process connections. This also simplifies installation, maintenance and repair of the stream selector valve.

Further features of the present invention will become apparent to those skilled in the art upon reviewing the following specification and attached drawings.

BRIEF DESCRIPTION OF THE DRAWINGS

FIG. 1 is a side view of a stream selector constructed according to the principles of the present invention;

FIG. 2 is a top view of the stream selector of FIG. 1;

FIG. 3 is an end view taken from the left side of the stream selector of FIG. 2;

DETAILED DESCRIPTION OF THE PREFERRED EMBODIMENT

Figure 4:
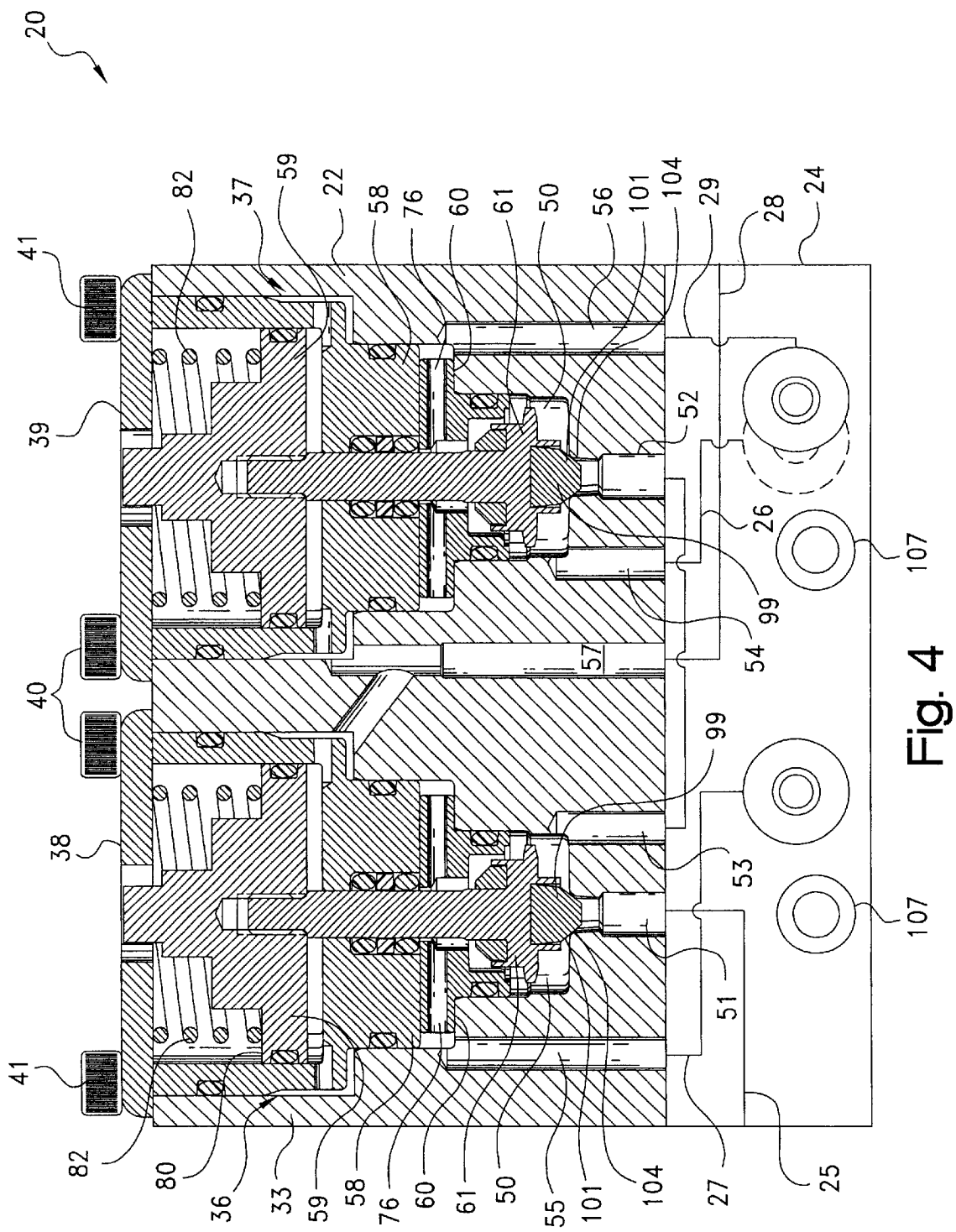
FIG. 4 is a multi-plate cross-sectional side view of the valve module of the stream selector taken substantially along the plane described by the lines 4—4 in FIG. 2.
Figure 5:
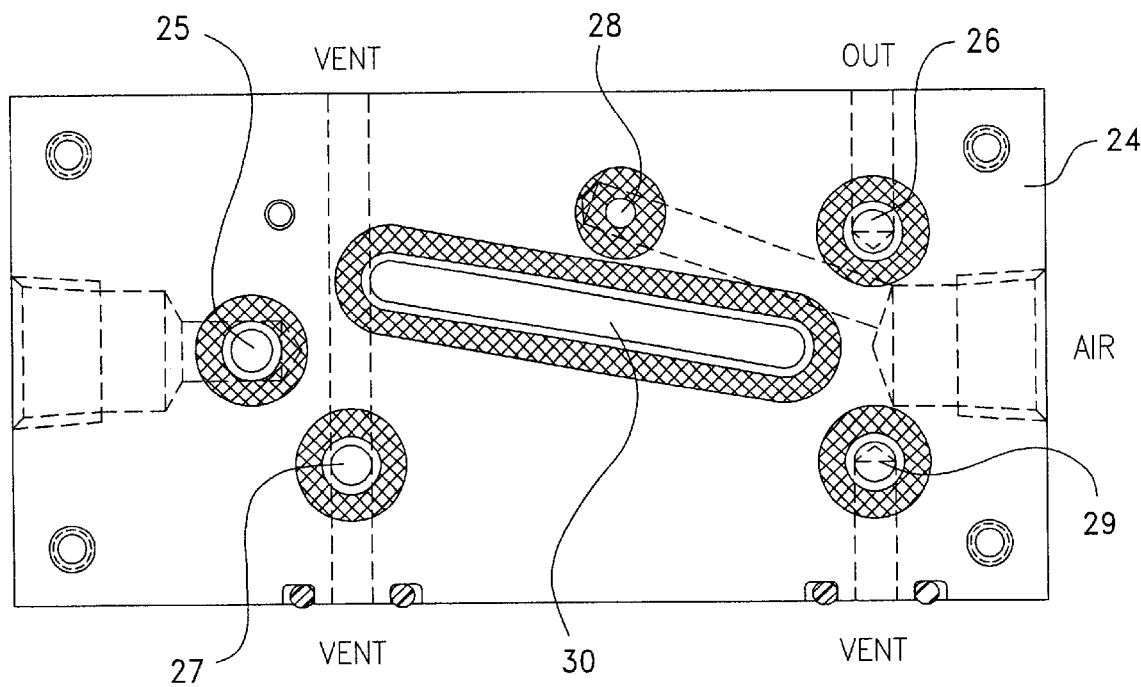
FIG. 5 is a top view of the base plate for the stream selector taken substantially along the plane described by the lines 5—5 of FIG. 1.

Referring to the drawings, and initially to FIGS. 1–3, a stream selector constructed according to the principles of the present invention is indicated generally at 20. The stream selector 20 includes a valve module 22 removably attachable to a base plate 24. Referring also to FIG. 4, the base plate 24 includes an inlet passage 25, an outlet passage 26, a first vent passage 27, an actuation passage 28, a second vent passage 29, and a common connection passage or channel 30, as will be described herein in more detail. The passages 25–29 all have one end that opens to the top flat surface 31 of the base plate adjacent the valve module, as shown in FIG. 5. Common passage 30 is open along the length of the passage. Appropriate O-ring seals are provided in grooves in the upper surface 31 of the base plate surrounding the openings to provide a fluid-tight seal with the flat lower surface 32 (FIG. 7) of the valve module.

The passages (25–29) all have other ends that open along the end and side surfaces of the base plate. For example, referring to FIGS. 4 and 5, the inlet passage 25 opens to one end of the base plate; the actuation passage 28 opens to the opposite end of the base plate; the first vent passage 27 opens along both sides of the base plate, the second vent passage 29 opens to one side of the base plate; and the outlet passage 26 opens to the other side of the base plate, preferably at approximately the same location (but on the opposite side) as second vent passage 29. Of course, this is only one example of the flow paths through the base plate, and the passages could have other configurations depending upon the particular application.

Figure 6:
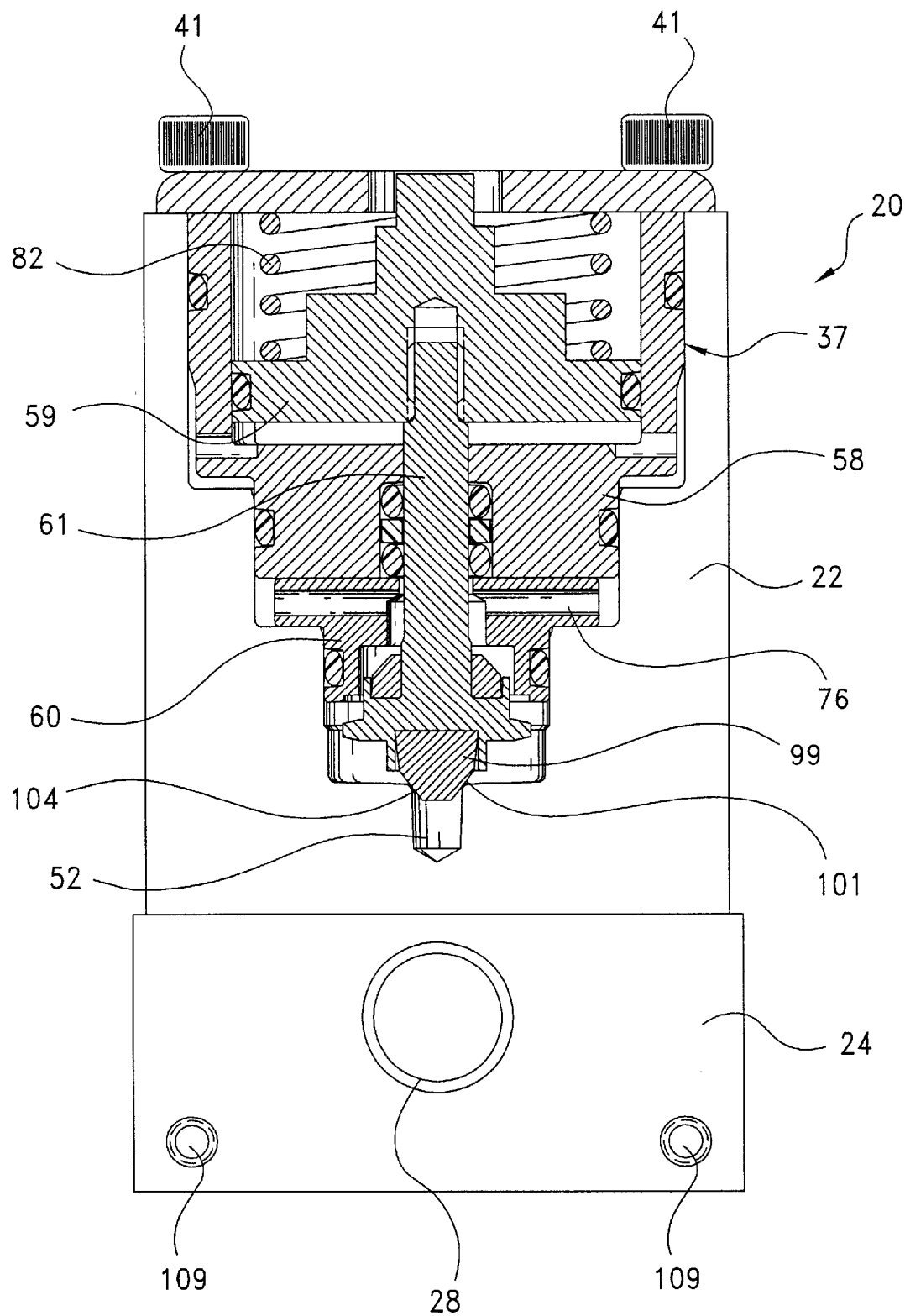
FIG. 6 is a cross-sectional end view of the valve module taken substantially along the plane described by the lines 6—6 in FIG. 2.
Figure 7:
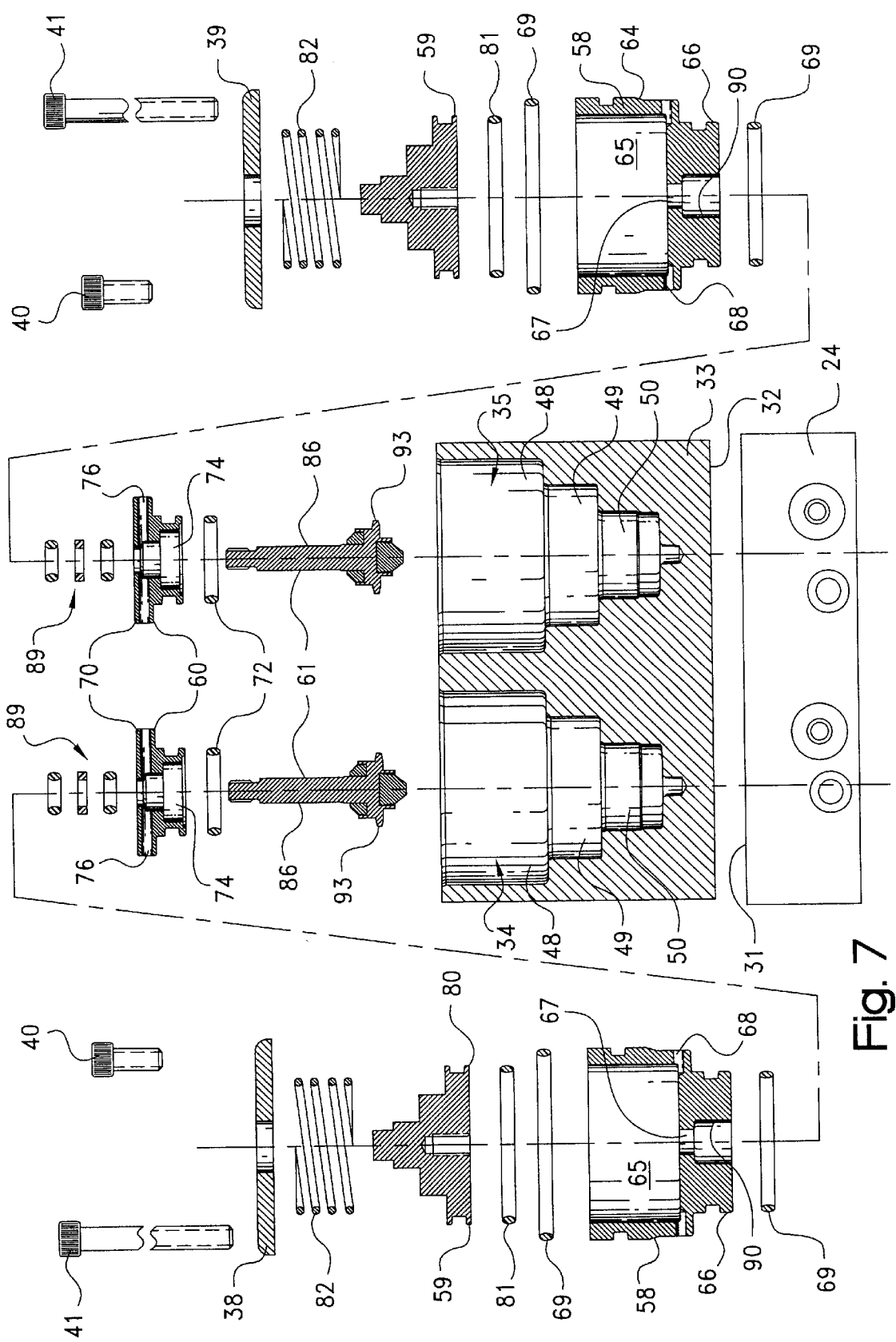
FIG. 7 is an exploded view of the stream selector of FIG. 4.

Each module includes a module body 33 having a pair of valve receiving cavities 34, 35. A valve assembly is received in each valve cavity. That is, valve assembly 36 is received in valve cavity 34, while valve assembly 37 is received in valve cavity 35. Covers 38, 39 are provided to enclose each valve assembly 36, 37, respectively, in a valve cavity. Referring also to FIGS. 6 and 7, threaded bolts 40 extend partway into the module body 33 to connect the covers 38, 39 to the module body; while threaded bolts 41 are longer and extend entirely through the module body 33 to the base plate 24 to removably connect the module to the base plate. With the module so connected, the lower flat surface 32 of the module in adjacent, surface-to-surface relation to the upper flat surface 31 of the base plate. While not shown, other appropriate means (clamps, etc.) could alternatively or additionally be used to removably attach the module to the base plate, as should be appreciated by those of ordinary skill in the art.

As shown in FIGS. 4–7, each valve receiving cavity 34, 35 is preferably identical, and includes an enlarged actuation cavity portion 48, a slightly (radially) smaller vent cavity portion 49, and a still slightly (radially) smaller control cavity portion 50, with the vent cavity portion 49 located between the actuation cavity portion 48 and the control cavity portion 50. Inlet passages 51, 52 are provided through module body 33 from the lower surface 32 directly into the central portion of the control chamber portion 50 for each valve receiving cavity. Inlet passage 51 for valve assembly 36 is fluidly aligned and connected to inlet passage 25 in base plate 24; while inlet passage 52 for valve assembly 37 is fluidly aligned with one end of common passage 30. Outlet passages 53, 54 are similarly provided from the lower surface 32 into the side of each control chamber portion of each valve receiving cavity. Outlet passage 53 for valve assembly 36 is fluidly aligned with the other end of common passage 30; while outlet passage 54 for valve assembly 37 is fluidly aligned with outlet passage 26 in base plate 24. Common passage 30 directly fluidly connects the outlet passage 53 of valve assembly 36 with the inlet passage 52 of valve assembly 37.

Vent passages 55, 56 are similarly provided into the side of the vent cavity portion 49 of each valve receiving cavity. Vent passage 55 for valve assembly 36 is fluidly aligned with first vent passage 27 in the base plate 24; while vent passage 56 for valve assembly 37 is fluidly aligned with second vent passage 29 in base plate 24.

A common actuation passage 57 is provided for both valve assemblies, and extends from the actuation chamber 48 of each valve receiving cavity 34, 35, where it is fluidly aligned with the actuation passage 28 in the base plate.

The valve assemblies are also preferably identical for ease of manufacture and assembly, although, of course, this could also be different. Each includes a valve body 58, a piston 59 moveably disposed in the valve body, a valve bonnet 60 and a valve poppet 61. The valve body 58 includes a cylindrical wall portion 64 defining a central piston receiving cavity 65. The cylindrical wall portion 64 is closely received in the actuation cavity portion 48. The valve body 58 further includes a cylindrical base portion 66 which is closely received in the vent cavity portion 49. The base portion 66 includes a central through-bore 67, and one or more radial passages 68 at the junction between the wall portion 64 and the base portion 66, all opening into piston receiving cavity 65. Appropriate O-ring seals 69 are provided in grooves in valve body 58 to provide a fluid-tight seal between valve body 58 and the module body 33.

Valve bonnet 60 has a cylindrical body portion 70 closely received in vent cavity portion 49, and a cylindrical base portion 71 closely received in control cavity portion 50. Covers 38 and 39 retain the valve bonnet 60 and valve body 58 securely in each valve receiving cavity, such that these components are fixed relative to the module body 33. An O-ring seal 72 is received in a groove in the valve bonnet 60 and provides a fluid-tight seal between the bonnet 60 and the module body 33. Bonnet 60 also includes a central through-bore 74, and one or more radial passages 76 which fluidly connect with the through-bore.

The piston 59 has a cylindrical base 80 closely received in the piston receiving cavity 65 of the valve body 58. Piston 59 is allowed to move axially within cavity 65, and includes a groove receiving an O-ring seal 81 for providing a fluid-tight seal between the piston and the valve body 58.

The upper surface of the base 80 provides a spring stop for a compression spring 82. As best shown in FIG. 4, the compression spring 82 is located between the base 80 and a respective cover 38, 39 and normally urges the piston 59 downwardly toward the base 66 of the valve body 58.

Figure 8:
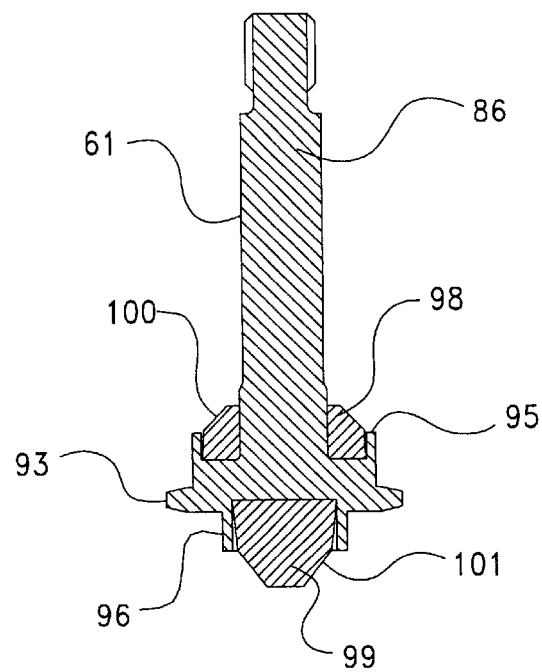
FIG. 8 is a cross-sectional side view of the poppet valve for the valve module.

Referring also to FIGS. 7 and 8, the poppet valve 61 has an elongated cylindrical stem 86 which extends through the passage 74 in the valve bonnet 60 and through the bore 67 in the valve body 58. The stem extends upwardly to a threaded connection with the piston 59, and as such, the piston and poppet valve move axially in conjunction with one another. A series of O-rings 89 or other packing is provided in a counterbore 90 in the bore 67 of the valve body 58 to provide a fluid-tight seal between the stem 86 of the poppet valve and the valve body 58.

The poppet valve 61 further has a cylindrical valve head 93 at the lower end of the valve stem. The valve head is located in the control cavity portion 50 of the valve receiving cavity. As shown particularly in FIG. 8, an annular sleeve 95 extends outwardly away from one (upper or rear) surface of the valve head 93 toward the valve bonnet 60; while a similar annular sleeve 96 extends outwardly (downwardly) away from the opposite (lower or front) surface of the valve head 93 toward the inlet passages 51, 52, respectively. Sleeves 95, 96 define seal holders.

An upper or rear plug seal 98 is received in upper/rear seal holder 95, while a lower or front plug seal 99 is received in lower/front seal holder 96. Each plug seal is preferably formed from PCTFE, or other appropriate resilient polymer. Plug seal 98 has an annular configuration and is closely received around stem 86 and is received, preferably with a friction fit, in seal holder 95. Plug seal 99 has a solid cylindrical configuration and is closely received, preferably with a friction fit, in seal holder 96. Seal holders 95, 96 can be crimped to facilitate retaining the plug seals 98, 99, respectively. Each plug seal 98, 99 has an outwardly-facing tapered surface 100, 101, respectively, and is designed to sit squarely against a valve seat. Specifically, when the module is in a non-actuated condition (as shown in, e.g., FIGS. 4 and 6), the tapered surface 101 of lower seal 99 sits squarely against a valve seat 104 defined at the upper/inner end of inlet passage 51, 52, respectively, and provides a fluid-tight seal therewith. Likewise, when the module is in an actuated condition (as shown in, e.g., FIG. 9), the tapered surface 100 of the upper seal 98 sits squarely against a valve seat 105 defined at the lower/inner end of through-bore 74 in valve bonnet 60, and provides a fluid-tight seal therewith.

The operation of the module will now be described. It is typical and preferred that both valve assemblies in the module operate simultaneously, that is, in conjunction with one another. When the module is in its non-actuated condition (e.g., FIGS. 4 and 6), spring 82 forces the piston 59 in each valve assembly downwardly toward the valve body 58. The poppet valves are likewise pushed downwardly such that they seal the respective inlet passages 51 and 52. In this condition, fluid is prevented from flowing through the module. As the poppet valve is in a position where the upper seal 98 is spaced-apart from the valve seat 105, any fluid in the control cavity portion 50 vents through bore 74 in valve bonnet 60 (in the area surrounding the poppet valve stem 86), through radial passage 76 in the bonnet, to vent cavity 49 and then through vent passage 55 (for valve assembly 36) or vent passage 56 (for valve assembly 37). The vented fluid then flows through the respective vent passages 27, 29 in the base plate, which exhaust the fluid (typically to atmosphere).

Figure 9:
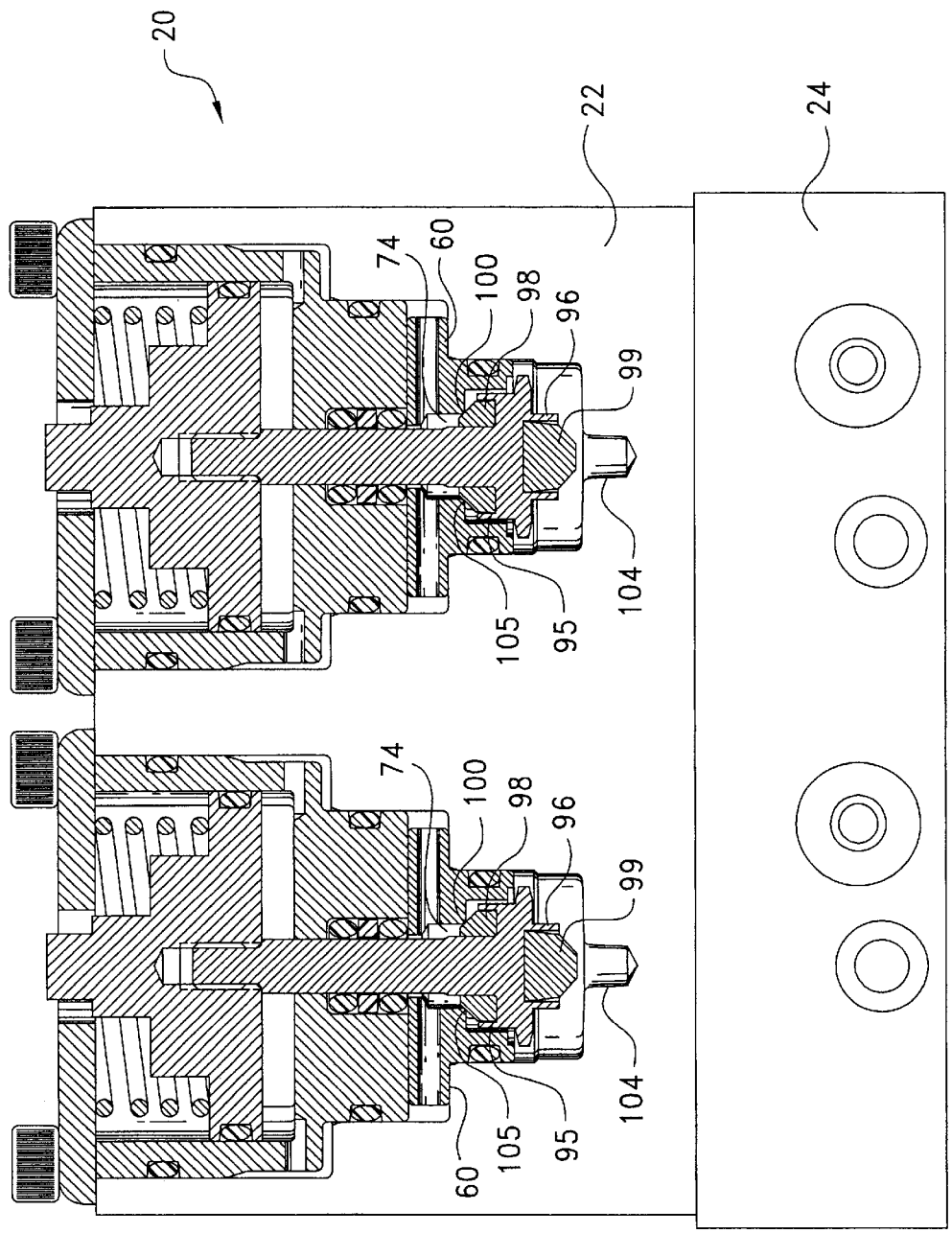
FIG. 9 is a cross-sectional side view of the valve module similar to FIG. 4, but showing the module in an actuated condition.

When the module is actuated, actuation fluid (e.g., compressed gas) is provided through actuation passage 28 in base plate 24 to common actuation passage 57 in the module body 33. The actuation fluid is directed into actuation cavity 48 of both valve assemblies, where it flows through ports 68 in valve body 58, and into the space between each valve body and the piston. The fluid is applied against the lower surface of the piston to force the piston upwardly against spring 82. When the pressure of the actuation fluid exceeds the pressure of the spring, the piston, and hence the valve poppet 61, moves upwardly in the module, such that the lower seal 99 moves away from the valve seat 104, and the upper valve seal 98 moves into sealing relation with the valve seat 105 for each assembly, as shown in FIG. 9. Fluid can pass from the inlet passages, into control cavity 50, and then out through outlet passage 53 (for valve assembly 36) or outlet passage 54 (for valve assembly 37). As should be appreciated, fluid applied through outlet passage 53 from valve assembly 36 flows through common passage 30 (FIG. 5) and directly into inlet passage 52 to valve assembly 37, where the fluid passes to outlet passage 54.

An intermediate mode can also be provided, where the seals 98, 99 are each spaced a short distance from their respective valve seats 104, 105. A complete purge of fluid occurs from the module in this condition.

While it is described above that passage 51 is an inlet passage and passage 53 is an outlet passage for valve assembly 36; and passage 52 is an inlet passage and passage 54 is an outlet passage for valve assembly 37, it should be appreciated that the inlet and outlet passages could be reversed, such that sample fluid is provided into passage 54 and out of passage 52 of valve assembly 37 and then into passage 53 and out of passage 51 of valve assembly 36. This can be accomplished by switching the fluid lines into base plate 24, or alternatively reconfiguring the passages 26, 27 and 30 in the base plate.

Figure 11:
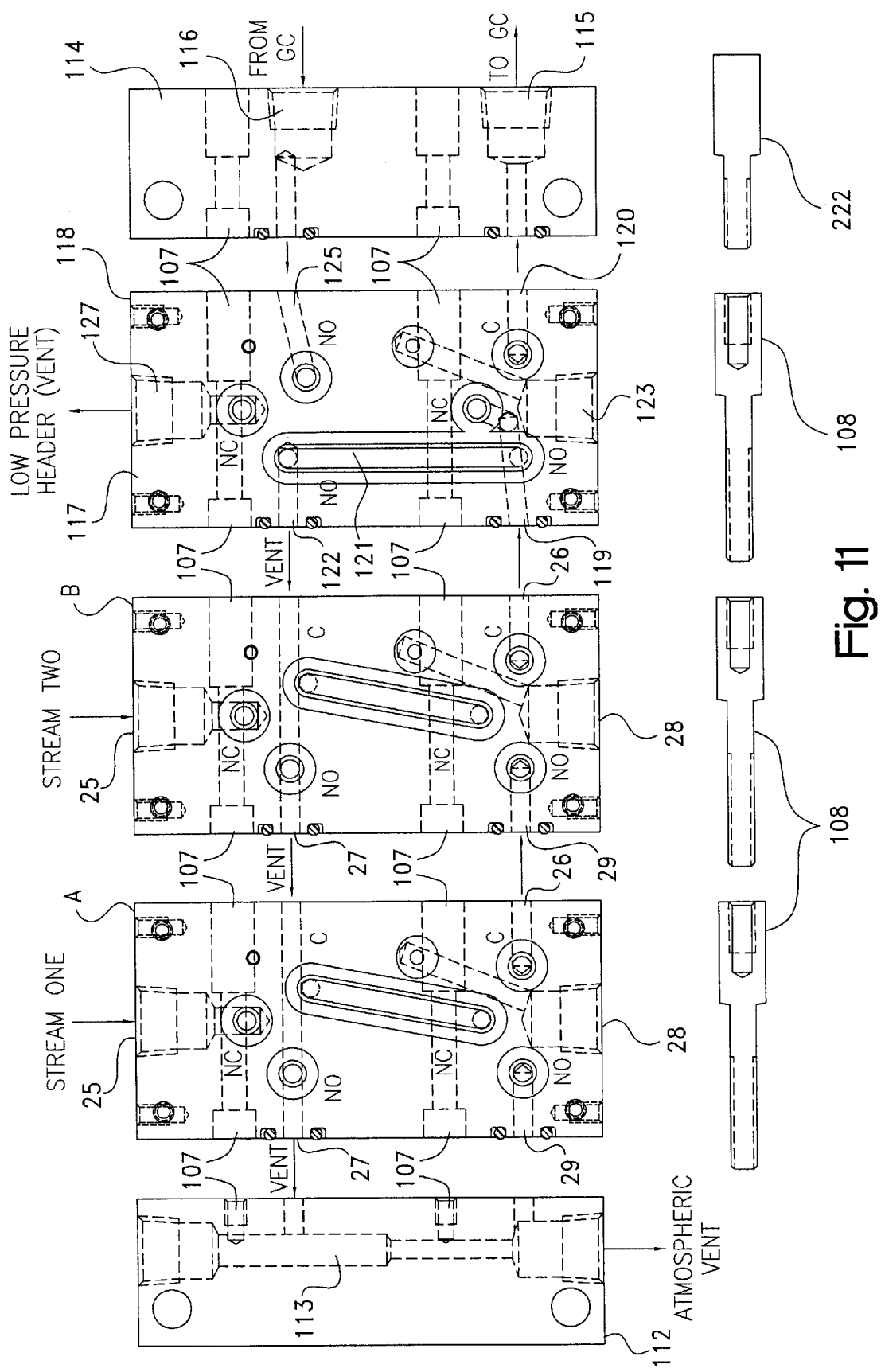
FIG. 11 is a schematic representation of the flow paths through multiple valve modules in a stream selector system.

One of the advantages of the present invention is that it is relatively simple to service the modules. Since the modules are individually attachable to the base plates, only one module need be removed at a time—without disturbing the other modules. With all the process connections for the liquid lines provided on the base plate, this makes it quick and easy to replace any particular module. In addition, horizontal through-bores 107 (FIG. 4) are provided through each base plate 24 to facilitate the securing of the modules adjacent one another. As shown in FIG. 11, appropriate bolts 108 can be inserted through the through-bores. The module/base plate combinations can also be easily removed and serviced and/or replaced simply by removing bolts 108, the air line (28 or 123) and only one liquid process connection (25 or 127). The side-by-side arrangement of the modules also allows the number of modules to be easily scaled (increased or decreased) depending upon the particular application.

Figure 15:
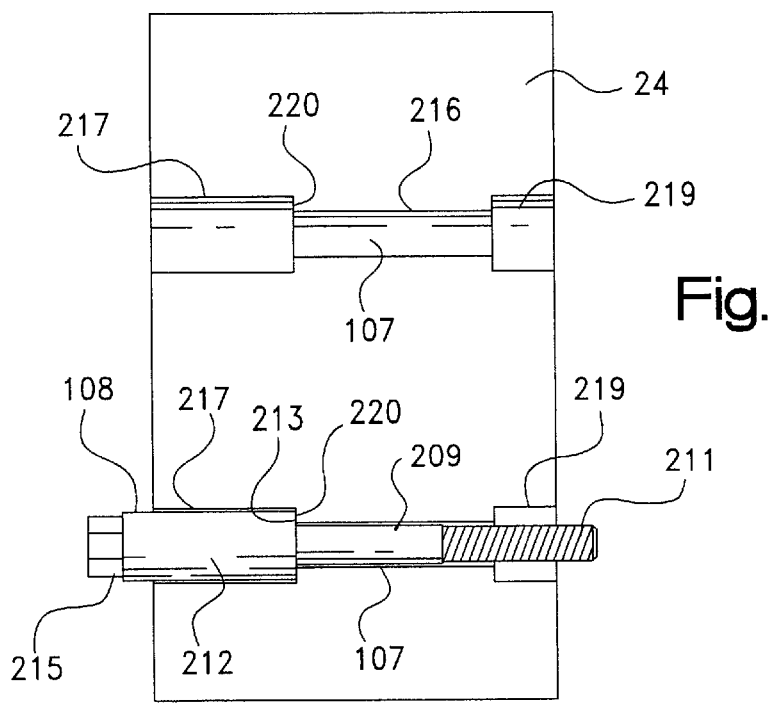
FIG. 15 is a top view of one of the base plates for the stream selector, illustrating a bolt assembled with the base plate.
Figure 16:
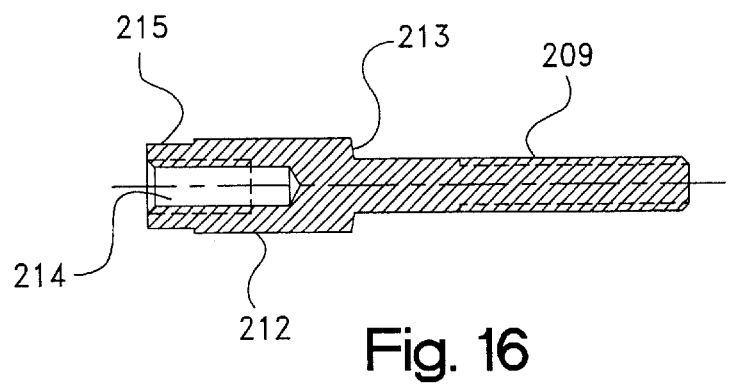
FIG. 16 is a cross-sectional side view of one of the bolts for the stream selector.
Figures 17, 18:
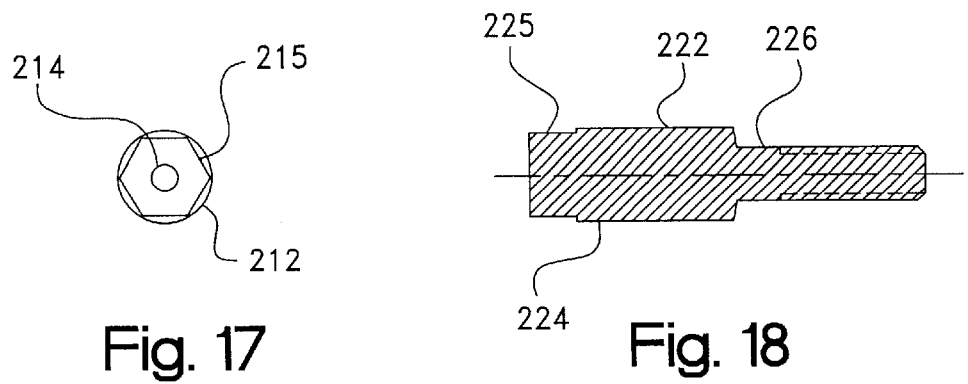
FIG. 17 is an end view of the bolt.
FIG. 18 is a cross-sectional side view of another of the bolts for the stream selector.

As shown in FIGS. 15 and 16, bolts 108 include an elongated shank 209, with a threaded portion 211 at one (distal) end of the bolt, and an enlarged head 212 at the other end of the bolt. An annular shoulder 213 radially connects the enlarged head 212 and the shank 209. A central threaded blind end bore 214 extends axially inward from the head end of the bolt, as can be seen in FIG. 17. Bore 214 is sized so as to receive a threaded shank 209 from an adjacent bolt.

Both the head 212 and shank 209 are generally smooth and cylindrical, and the end of the head 212 includes an external tool engaging portion 215 having a non-cylindrical geometry allowing a tool to grasp and rotate the bolt. As illustrated in FIG. 17, the tool engaging portion 215 can have a hex shape to fit a hex tool, although of course, other shapes are possible. While not shown, the tool engaging portion could also be provided internal to bore 214, rather than external.

Head 212 and shank 209 are sized so as to be closely received in throughbores 107 in the base plates. As can be seen in FIG. 15, throughbores 107 each include a main portion 216; a first enlarged end 217 with an inner cylindrical surface; and a second enlarged end 219, also with an inner cylindrical surface. An annular shoulder 220 radially interconnects first enlarged end 217 and main portion 216. Head 212 of bolt 108 is closely received in first enlarged end 217, with shoulder 213 engaging corresponding shoulder 220; while threaded portion 211 is received in second enlarged end 219. The head 212 and first enlarged end 217 are sized so that the tool engaging portion 215 and a portion of the cylindrical head extend outwardly from the throughbore 107, from one edge of the base plate. Likewise, the bolt is sized such that a portion of the end of shank 209 projects outwardly from the other side edge of the base plate. The second enlarged end 219 of the throughbore 107 is further sized so as to closely receive the tool engaging portion 215 and cylindrical head portion of an adjacent base plate, with the threaded shank 209 of one bolt received in the threaded bore 214 of the adjacent bolt. The cylindrical head 212 and second enlarged end 219 locate and align the adjacent base plates together for a proper fit. The outwardly-projecting tool engaging portion 215 enables the assembler to engage the opposite end of the bolt with an appropriate tool, and tighten the one bolt to the other, and hence fix the one base plate to the other.

Once the bolt is properly tightened down within the throughbore to the adjacent bolt, a still further base plate can be assembled, by repeating the above assembly steps.

FIG. 18 illustrates a bolt 222 useful for the final base plate, where the bolt does not include a central bore. The bolt 222 in FIG. 18 is also illustrated as being somewhat smaller than the bolt 108 in FIGS. 15 and 16, but this is because the bolt is illustrated as being used with an end plate (see FIG. 11), which tends to be thinner than a base plate, however, this is not always the case, and it should be apparent that the length of the bolt will depend upon the dimensions of the plate it is used in. Bolt 222 in FIG. 18 is otherwise the same as bolt 108 illustrated in FIG. 16, and includes and enlarged head 224 with a tool engaging portion 225, and an elongated shank 226.

It is noted that a pair of bolts are illustrated as being used with the base plate 24 of FIG. 15, and while this is preferred, it is noted that only a single bolt, or more than two bolts, may be appropriate in certain situations.

As should be apparent from the above, the use of the bolts 108, 224 provides an easy and rapid method of assembling the base plates together, to further facilitate assembling the stream selector of the present invention.

Figure 10:
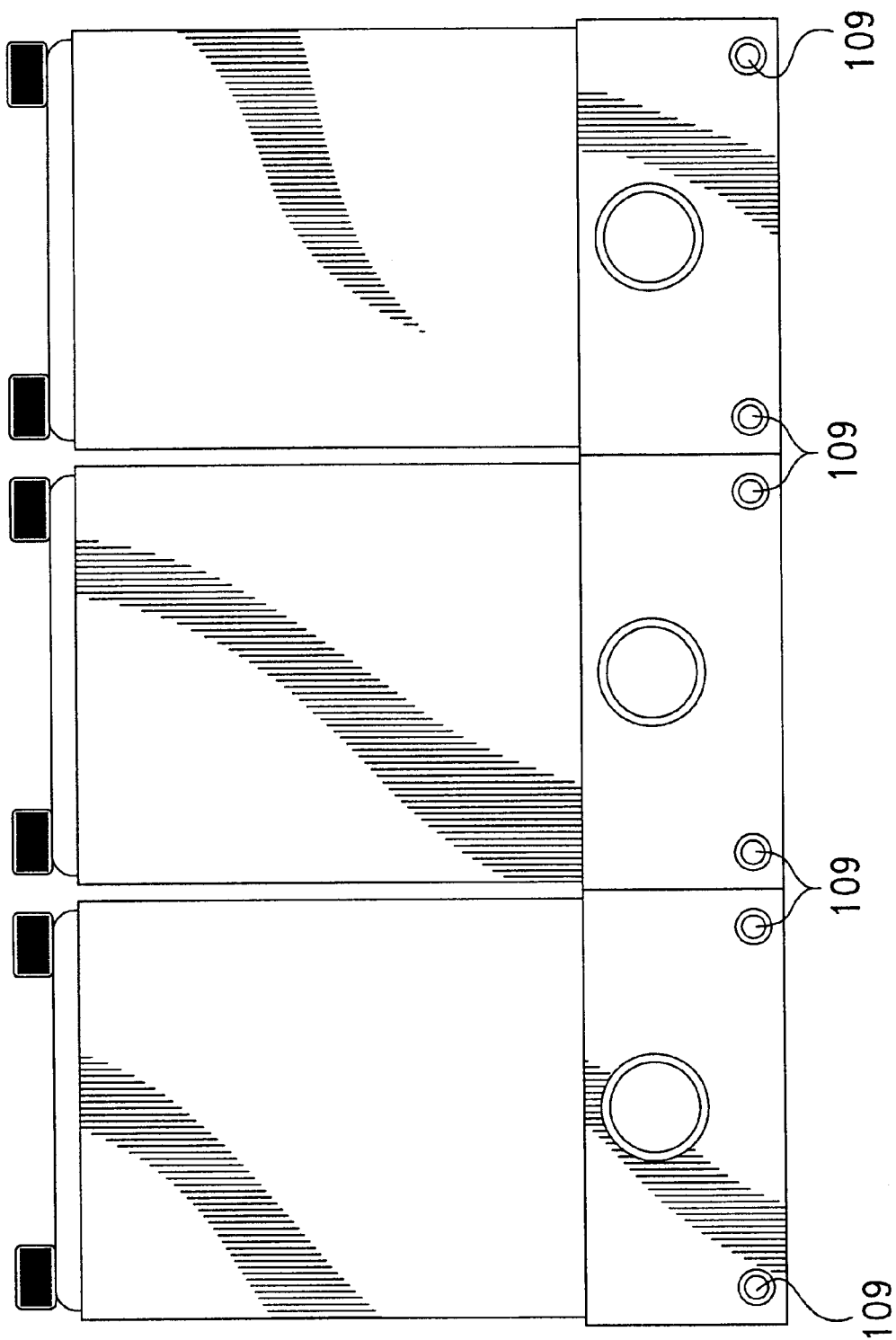
FIG. 10 is a side view of a series of modules for the stream selector mounted adjacent one another.

If necessary or desirable, additional support can be provided to the valve modules by inserting bolts (not shown) through threaded bores 109 (FIGS. 3, 6, 10) on base 24, and attaching the bolts to a support surface.

As shown in FIG. 11, each additional module is preferably connected to a previous module by fluidly connecting the common outlet passage 26 from the base plate in the first module to the normally-open vent passage 29 of the base plate in the adjacent module. This flow path addresses the issue of dead volume in the outlet header without adding an outlet loop. The vent passages 27 between adjacent modules are also aligned and fluidly connected. As indicated previously, passages 27 preferably open to the opposite side surfaces of the base plate at the same location. A first end plate 112 can be provided adjacent the upstream module "A" at one end of the module stack with a common vent passage 113 to atmosphere for both vent passages 29 and 27. Similarly, a second end plate 114 can be provided at the other end of the module stack with a passage 115 connecting with passage 26 in the downstream module B to pass gas to the analyzer. A passage 116 connects the gas flow from the analyzer back through the module stack. End plates 112, 114 facilitate mounting the modules at an appropriate location on the panel.

A low pressure header 117 can also be provided between the downstream module "B" and end plate 114. Header 117 includes a valve module having a pair of valve assemblies, preferably with the same structure and function as the assemblies described above. Header 117 also has a base plate 118, such as described previously, however, the passages through the base plate are different than as described above.

Specifically, the base plate 118 includes an inlet passage 119 which fluidly connects with outlet passage 26 of the adjacent, upstream module "B". Passage 119 is fluidly connected with the passage 52 of valve assembly 37 in the header module body. Passage 54 in the header module body is fluidly connected to outlet passage 120 in base plate 118, which is itself fluidly connected to passage 115 in the adjacent plate 114. The vent passage 56 in the module body is fluidly connected to one end of common passage 121. A further passage 122 has one end which is fluidly connected to the other end of common passage 121, and an opposite end which is fluidly connected to vent passage 27 in the adjacent module "B". Actuation passage 123 provides actuation gas to common actuation passage 57 in the module body. Actuation of the valve assembly 37 controls the flow of gas from inlet passage 119 to outlet passage 120. When the valve assembly 37 is closed, gas is vented back through the module stack via passages 27.

Likewise, passage 125 in base plate 118 is fluidly connected to passage 116 in end plate 114 and receives gas exiting from the analyzer. Passage 53 in valve assembly 36 is fluidly connected with passage 125. Passage 51 in valve assembly 36 is fluidly connected to passage 127, which leads to atmosphere or preferably, to a collection tank (not shown). Passage 55 in valve assembly 36 is fluidly connected to passage 121 in plate 118, which leads to passage 122. When the valve assembly 36 is activated, fluid flows from passage 125 to passage 127 and then to atmosphere or collection. When the valve is not activated, fluid flows from passage 125 to passage 122 to vent.

Figure 12:
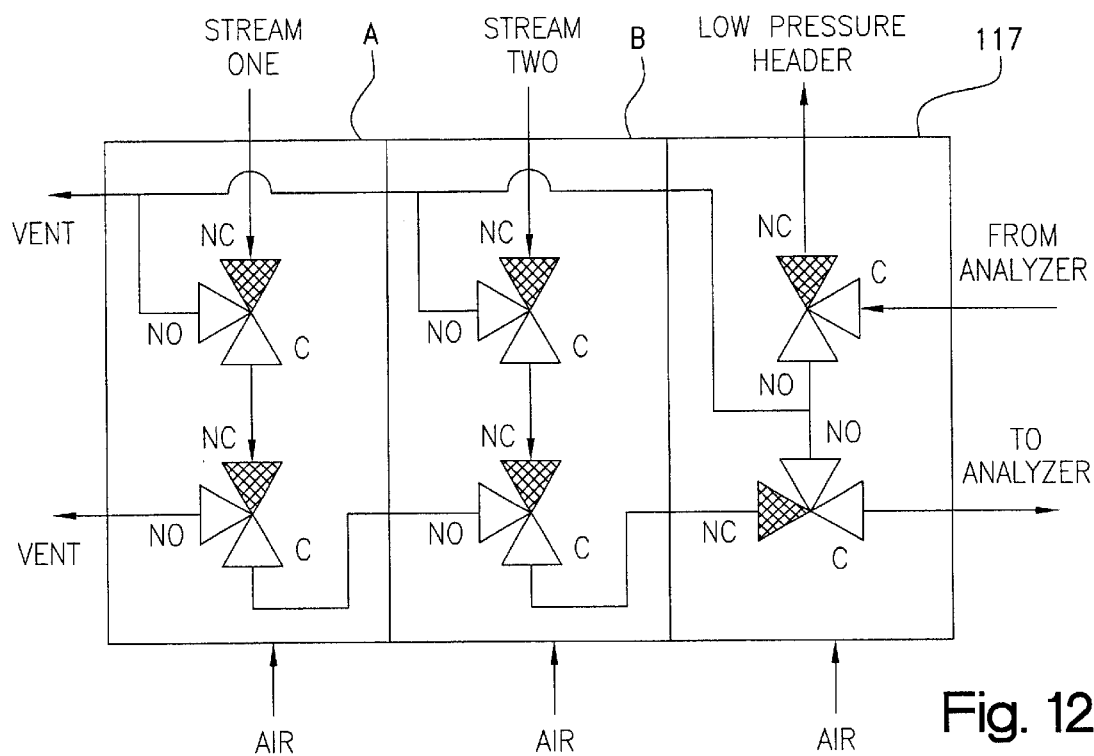
FIG. 12 is a schematic representation of the flow through a three module stream selector when neither of the valve modules are actuated.
Figure 13:
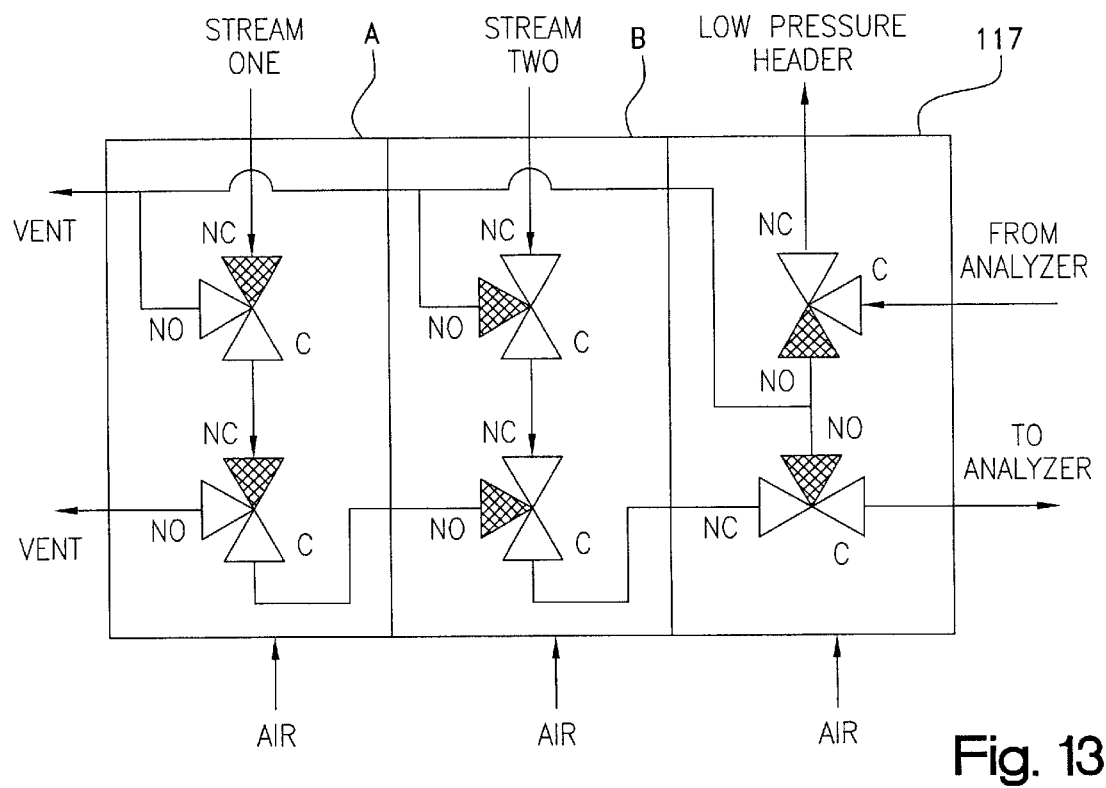
FIG. 13 is a schematic representation of the flow through a three module stream selector when one of the valve modules and the header module are actuated.

The flow paths through multiple modules "A" and "B" and the header 117 is shown schematically in FIGS. 12 and 13. When the modules and header are not actuated (FIG. 12), the seals in each module prevent fluid from passing through the respective modules. Any fluid leaking through the poppet valve seals is vented, and therefore does not contaminate the sample being analyzed. Any fluid from the analyzer is purged to vent. When one module (for example module B in FIG. 13), and the header 117 are actuated, the outlet of the module is applied through the header to the analyzer, while module A remains purged. The gas returning from the analyzer is collected or vented to atmosphere.

As such, the stream selector does not require a common outlet header to connect to the process analyzer. Rather, the outlet from the last module in the string of modules is connected to the analyzer. The previous process streams are fully vented before the introduction of a new process stream into the last module. The stream selector thereby prevents contamination of one sample with residual fluid from a previous sample, and has little dead volume. Still further, the stream selector has a compact size, and is relatively simple in construction. This also reduces installation, maintenance and repair costs. The seal plugs of the poppet valve are robust, long-lasting components that withstand repeated cycling without leaking. The modules each easily connect into and disconnect from the base plate, which itself carries all the process connections. This also simplifies installation, maintenance and repair of the stream selector valve.

Figure 14:
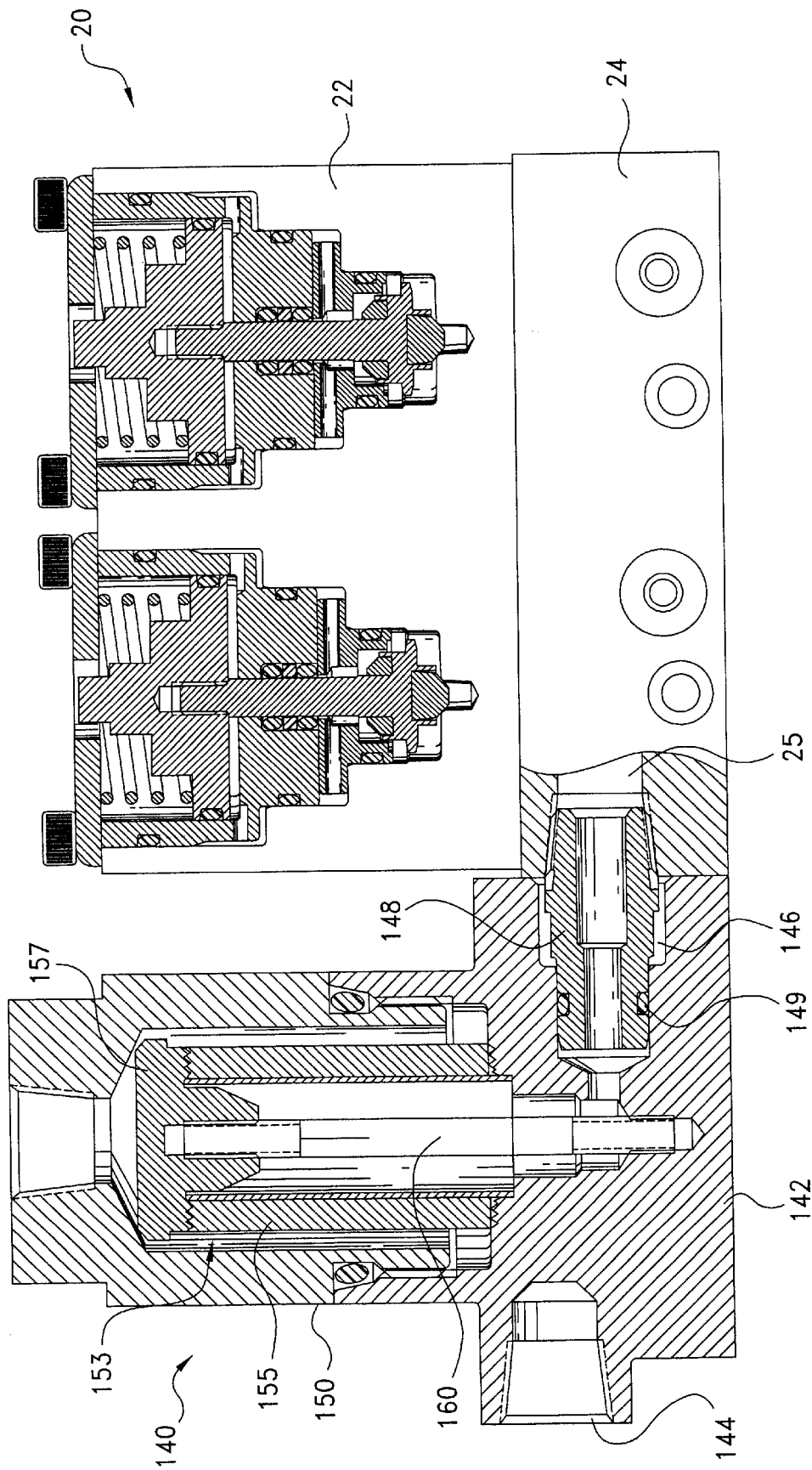
FIG. 14 is a side view of a valve module in partial cross-section, showing a filter assembly attached to the stream selector.

An additional feature that can be easily provided with one or more of the valve modules is a filter assembly, indicated generally at 140 in FIG. 14. The filter assembly 140 provides a filtration function for fluid received in inlet passage 25. Filter assembly 140 includes a body 142 having an inlet port 144 and an outlet port 146. Inlet port 144 has appropriate connections (e.g., screw threads) to allow the filter assembly to be easily connected within the fluid system. The outlet passage 146 receives a fitting/regulator 148, which is connected, such as with cooperating threads, to the inlet passage 25, and is received with a close fit in passage 146. An O-ring seal 149 is received around the inner end of fitting 146 and provides a fluid-tight seal within passage 146. The filter body 142 includes an elongated removable filter canister 150 which receives a filter element or cartridge, indicated generally at 153. Filter cartridge 153 includes an annular filter media 155 formed of an appropriate material, and an upper seal or end cap 157. End cap 157 receives a central rod 160, which removably attaches the end cap to the body 142, and allows the filter element to be replaced when spent. To this end, canister 150 is removably connected such as by cooperating screw threads, to body 142. When canister 150 is removed, end cap 157 can be screwed off from rod 160, and the element inspected and replaced if necessary. Fluid flows from inlet 144, upwardly in the peripheral chamber between the canister 150 and the media 155, radially inward through the media, and then downwardly and outwardly through fitting/regulator 148 to the module. In this manner, the sample can be filtered prior to passing through he module and passing onto the analyzer.

The principles, preferred embodiments and modes of operation of the present invention have been described in the foregoing specification. The invention which is intended to be protected herein should not, however, be construed as limited to the particular form described as it is to be regarded as illustrative rather than restrictive. Variations and changes may be made by those skilled in the art without departing from the scope and spirit of the invention as set forth in the appended claims.

What is claimed is:

1. A valve module for a stream selector, the valve module including:

a module body having a valve receiving cavity, the valve receiving cavity including a control chamber portion, a vent chamber portion, and an actuation chamber portion, with the vent chamber portion being located between the control chamber portion and the actuation chamber portion; the module body including a) inlet and outlet passages into the control chamber portion with one of said inlet and outlet passages aligned along a geometric axis of the module body and defining an annular front valve seat into the control chamber portion; b) a vent passage into the vent chamber portion; and c) an actuation passage into the actuation chamber portion; and a valve assembly received in the valve receiving cavity, the valve assembly including i) a valve body having a piston receiving cavity and an axially extending central through-bore into the piston receiving cavity, the valve body received in the actuation chamber portion of the valve receiving cavity, a piston moveably received in the piston receiving cavity of the valve body, the piston and valve body defining an actuation chamber therebetween, the actuation passage fluidly connected to the actuation chamber through a port in the valve body; ii) a bonnet received in the vent chamber portion of the valve receiving cavity, the bonnet having a vent cavity, the vent passage fluidly connected to the vent cavity, the vent passage including an annular rear valve seat and an axially-extending central through-bore fluidly connecting the outlet passage and the vent cavity and co-axially aligned with the central through-bore in the valve body; and iii) a poppet valve having a valve head disposed in the control chamber portion, the valve head having an annular rear seal holder facing toward the bonnet and an annular front seal holder facing away from the bonnet and toward the one of the inlet and outlet passages, the poppet valve further including a stem extending axially through the through-bore in the bonnet and the through-bore in the valve body to a fixed connection with the piston such that the valve head of the poppet valve moves axially in conjunction with the axial movement of the piston, the poppet valve including an annular rear seal plug received around the poppet valve stem and within the annular rear seal holder of the valve head, the rear seal plug adapted to seal against the rear valve seat surrounding the poppet stem during movement of the poppet valve in a rearward axial direction, and the poppet valve also including a cylindrical front seal plug received in the annular front seal holder, the front seal adapted to seal against the front valve seat during movement of the poppet valve in a forward axial direction.

2. The valve module as in claim 1, wherein said rear seal plug includes a tapered outer surface to facilitate sealing with the rear valve seat.

3. The valve module as in claim 2, wherein the rear seal plug includes a cylindrical outer surface closely received with a friction fit in the rear seal holder of the valve head.

4. The valve module as in claim 1, wherein the front seal plug has a solid disk-shaped configuration.

5. The valve module as in claim 4, wherein the front seal plug includes a tapered outer surface to facilitate sealing with the front valve seat.

6. The valve module as in claim 5, wherein the front seal plug includes a cylindrical outer surface closely received with a friction fit in the front seal holder of the valve head.

7. The valve module as in claim 1, wherein said front seal plug and said rear seal plug are both located in the control chamber portion of the valve receiving cavity.

* * * * *